US010888541B2

(12) United States Patent
Adams

(10) Patent No.: US 10,888,541 B2
(45) Date of Patent: Jan. 12, 2021

(54) METHOD AND COMPOSITIONS FOR TREATMENT AND PREVENTION OF BROAD SPECTRUM VIRUS AILMENTS COMPRISING A CALCIUM CHANNEL BLOCKER OR A CALMODULIN BLOCKER

(71) Applicant: DR. KENNETH ADAMS MEDICINE PROFESSIONAL CORPORATION, Toronto (CA)

(72) Inventor: Kenneth W. Adams, North York (CA)

(73) Assignee: DR. KENNETH ADAMS MEDICINE PROFESSIONAL CORPORATION, Toronto (CA)

( * ) Notice: Subject to any disclaimer, the term of this patent is extended or adjusted under 35 U.S.C. 154(b) by 0 days.

(21) Appl. No.: 16/423,225

(22) Filed: May 28, 2019

(65) Prior Publication Data

US 2019/0274992 A1    Sep. 12, 2019

Related U.S. Application Data

(63) Continuation of application No. 13/513,639, filed as application No. PCT/CA2010/001926 on Dec. 3, 2010, now Pat. No. 10,350,190.

(30) Foreign Application Priority Data

Dec. 3, 2009   (CA) ..................................... 2687013

(51) Int. Cl.
| | | |
|---|---|---|
| *A61K 31/277* | (2006.01) | |
| *A61K 31/00* | (2006.01) | |
| *A61K 31/4422* | (2006.01) | |
| *A61K 31/5415* | (2006.01) | |
| *A61K 31/554* | (2006.01) | |

(52) U.S. Cl.
CPC ............ *A61K 31/277* (2013.01); *A61K 31/00* (2013.01); *A61K 31/4422* (2013.01); *A61K 31/5415* (2013.01); *A61K 31/554* (2013.01)

(58) Field of Classification Search
CPC .. A61K 31/277; A61K 31/00; A61K 31/4422; A61K 31/5415; A61K 31/554
See application file for complete search history.

(56) References Cited

U.S. PATENT DOCUMENTS

| | | | |
|---|---|---|---|
| 4,663,317 | A | 5/1987 | Albrecht |
| 4,800,081 | A | 1/1989 | Albrecht |
| 4,849,412 | A | 7/1989 | Albrecht |
| 2003/0055036 | A1 | 3/2003 | Werner et al. |
| 2003/0229082 | A1 | 12/2003 | James et al. |
| 2005/0080122 | A1 | 4/2005 | Anderson |
| 2005/0209289 | A1 | 9/2005 | Talarico |
| 2005/0245502 | A1 | 11/2005 | Keller |

FOREIGN PATENT DOCUMENTS

| | | |
|---|---|---|
| CA | 2427757 A1 | 5/2002 |
| CA | 2 474 821 A1 | 8/2003 |
| JP | 04368338 | 12/1992 |
| WO | 87/00047 | 1/1987 |
| WO | 07008665 A1 | 1/2007 |
| WO | 10026602 A2 | 3/2010 |

OTHER PUBLICATIONS

Minnesota Health (Minnesota Department of Health Infection Control Fact Sheet, 2006) (Year: 2006).*
MMWR document (Arch Dermatol vol. 134, May 1998). (Year: 1998).*
Amaral et al., "Enhanced killing of intracellular multidrug-resistant Mycobacterium tuberculosis by compounds that affect the activity of efflux pumps". Journal of Antimicrobial Chemotherapy. 2007, V. 59, pp. 1237-1246.
Miadonna et al., "Effect of verapamil on allergen-induced asthma in patients with respiratory allergy". Annals of Allergy, Asthma and Immunology. 1983, V. 51, pp. 201-204.
De La Rocque et al., "Inhibition of human LAK-cell activity by the antidepressant trifluoperazine". Immunopharmacology. 1995, V. 29, pp. 1-10.
Marone et al., "Inhibition of histamine release from human basophils in vitro by calmodulin antagonists". Clinical Immonology and Immunopathology. 1983, V. 23, pp. 334-340.
Greenberg (Arch Intern Med, 163, Feb. 10, 2003).
National Diabetes Education Program (Diabetes Medication Supplement, 2007).
Thompson, (2009 (https://www.bami.us/Influenza/InfluenzaAbout.html).
Nugent et al. (Archives of Virology, 81, 163-170, 1984).
Eccles (Lancet Infect Dis 2005, 5, 718-725).
European Search Report dated Apr. 19, 2013 in European Patent Application No. 10834131.4, pp. 1-10.
International Preliminary Report on Patentability issued in parent international application No. PCT/CA2010/001926, dated Jun. 5, 2012, pp. 1-9.
Verapamil—FDA prescribing information, side effects and uses, www.drugs.com, Mar. 11, 2016, pp. 1-10.
Megarbane, et. al., "Predictors of mortality in Verapamil overdose: Usefulness of Serum Verapamil concentrations," Basic and Clinical Pharacology and Toxicology, 108, pp. 385-389, Nov. 29, 2010.

(Continued)

*Primary Examiner* — Umamaheswari Ramachandran
(74) *Attorney, Agent, or Firm* — Jeffrey S. Melcher; Melcher Patent Law PLLC

(57) ABSTRACT

In the broadest aspect, the invention provides a composition for and a method of prophylactic and/or therapeutic treatment of a animal/mammal for any viral disease, mixed bacterial and viral infections, bacterial infections, bacterial endotoxins, bacterial exotoxins, autoimmune diseases, and cellular or humoral mediated allergic conditions that is caused by any virus that relies on the maintenance of specific calcium ion concentrations for the post ribosomal RNA synthesis processing of viral protein translation, transportation and processing of viral structural components by utilizing a therapeutic amount of a blocker selected from the group consisting of a calcium channel blocker, a metabolite thereof, a calmodulin blocker and a metabolite thereof, and a pharmaceutical acceptable diluent or carrier; and/or is caused by damage to the animal/mammal by a pathological immune response to antigens.

5 Claims, No Drawings

(56) References Cited

OTHER PUBLICATIONS

Schwartz, "Acute and chronic pharmacodynamic interaction of verapamil and digoxin in atrial fabrillation," Circulation, VCol. 65, No. 6, Jun. 1982, pp. 1163-1170, http://circ.ahajournals.org/content/65/6/1163.citation.

Verelan PM capsules (verapamil hydrochloride) product sheets. Rx only PC3810, https://dailymed.nlm.nih_gov/dailymed/archives/fdaDrugInfo_cfm?archiveid= 1642.

CARDIZEM® (diltiazem hydrochloride) Direct Compression Tablets, Rx Data Sheet, Reference ID: 4016246, 11, 2016, pp. 1-10.

Cardizem LA (Diltiazem): Uses, Dosage, Side Effects, Interactions, Warning, Data Sheet, https://www.rxlist.com/cardizem-la-drug.htm, Jun. 29, 2020, pp. 1-11.

Dabrowska, How FDA Approves Drugs and Regulates Their Safety and Effectiveness, Congressional Research Service, 7-5700, www.crs.gov, R41983, May 8, 2018, pp. 1-31.

Ibister, Delayed asystolic cardiac arrest after diltiazem overdose; resuscitation with high dose intravenous calcium, Emerg Med J 2002;19:355-357, www.emjonline.com.

Roper, et. al., Fatal diltiazem overdose: report of four cases and review of the literature, the Fellowship of Postgraduate Medicine, 1993, Postgrad Med J (1993) 69, 474-476.

\* cited by examiner

METHOD AND COMPOSITIONS FOR TREATMENT AND PREVENTION OF BROAD SPECTRUM VIRUS AILMENTS COMPRISING A CALCIUM CHANNEL BLOCKER OR A CALMODULIN BLOCKER

FIELD OF THE INVENTION

The invention relates to methods and compositions for the treatment and prevention of broad spectrum of viral ailments, mixed bacterial and viral infections, bacterial infections, bacterial endotoxins, bacterial exotoxins, autoimmune diseases, and cellular or humoral mediated allergic conditions comprising a therapeutically effective amount of a blocker selected from the group consisting of a calcium channel blocker, a metabolite thereof, a calmodulin blocker and a metabolite thereof, and a pharmaceutical acceptable diluent or carrier.

SUMMARY OF THE INVENTION

A novel class of antiviral compounds has now been discovered which has been found to exhibit a particularly favorable broad spectrum of antiviral properties through all classes of viruses. The inventor has discovered that pharmaceutical compositions comprising a blocker selected from the group consisting of calcium channel blockers, metabolites thereof, calmodulin blockers and metabolites thereof that have been used to treat medical conditions unrelated to viral infections can effectively suppress intracellular replication of multiple viral species and prevent and treat diseases caused by a wide spectrum of acute or chronic viral infection. In addition to direct antiviral effects due to the suppression of viral replication and suppression of viral release from infected host cells, the inventor has also observed that these agents also have a beneficial inhibitory effect upon the host immune response to suppress the severity of the host's immune response to viral as well as other foreign antigens.

Since a significant portion of the pathologic damage done to the host during an infection or other types pathological diseases are a result damage to the host tissues from the immune systems indiscriminant damage to healthy and often uninfected host cells near or remote to the site of infection. These pharmaceutical compositions comprising a blocker selected from the group consisting of calcium channel blockers, metabolites thereof, calmodulin blockers and metabolites thereof also help protect the host from other exaggerated pathological conditions such as bacterial infections, bacterial exotoxins and endotoxins.

As a result these agents afford special protective benefits for isolated bacterial infections, mixed bacterial infections, isolated viral infections, mixed viral infections, mixed/combined/superimposed viral and bacterial infections.

As well these agents can be beneficial for other non-infectious diseases or pathological states such as autoimmune processes psoriasis, autoimmune thryroiditis, autoimmune neuritis, autoimmune pericarditis, autoimmune pneumonitis, or any other type of autoimmune process.

As well these agents can be beneficial for other non-infectious diseases or pathological states such as cell mediated allergic reactions to latex gloves, nickel or other metal allergies, or any other pathological immune response.

These are all examples of pathological conditions in animals of when the animals own immune response becomes excessive, and instead of protecting the animal, is actually damaging to the animal. This reduction in inflammation and damage to host is theorized by the inventor to be potentially an inhibitory effect of calcium channel blockers and calmodulin blockers on the movement and migration of inflammatory cells involved in the host response to these antigen into the sites of the pathologic or exaggerated immune response.

Thus, the invention provides methods and compositions for the treatment and prevention of broad spectrum infectious, inflammatory and autoimmune ailments in human beings.

In the broadest aspect the invention provides a composition for and a method of prophylactic and/or therapeutic treatment of a mammal for any viral disease that is caused by any virus that relies on the maintenance of specific calcium ion concentrations for the post ribosomal RNA to protein translation transportation and processing of viral structural components by utilizing a therapeutic amount of a blocker selected from the group consisting of a calcium channel blocker, a metabolite thereof, a calmodulin blocker and a metabolite thereof, and a pharmaceutical acceptable diluent or carrier.

Accordingly, in one aspect, the invention provides a pharmaceutical composition for the treatment and prevention of broad spectrum virus ailments, mixed bacterial and viral infections, bacterial infections, bacterial endotoxins, bacterial exotoxins, autoimmune diseases, and cellular or humoral mediated allergic conditions in animals and human beings, said composition comprising a therapeutically effective amount of a blocker selected from the group consisting of a calcium channel blocker, a metabolite thereof, a calmodulin blocker and a metabolite thereof, and a pharmaceutical acceptable diluent or carrier.

Preferably, the calcium channel blocker is verapamil, diltiazem or felodipine; and the calmodulin blocker is trifluoperazine.

Preferably, the composition is in the form of a cream, spray, aerosol, powder, liquid for nebulization, gel, ointment or patch.

Preferably, the composition is in the form of a tablet, a sustained release formulation for systemic use.

Preferably, the composition is in the form of a sterile solution for parenteral injection.

In a still yet further aspect, the invention provides a method of manufacturing a medicament intended for the prevention, and treatment of viral infections characterized in that the medicament is a blocker selected from the group consisting of a calcium channel blocker, a metabolite thereof, a calmodulin blocker and a metabolite thereof; and admixed with a pharmaceutical acceptable diluent or carrier.

Preferably, the blocker is selected from verapamil, diltiazem, felodipine and trifluoperazine.

Kits comprising pharmaceutical compositions of the invention formulated in sterile unit dosage forms suitable for administration to patients, includes instructions for use in written, oral, videotape, compact disc, other digital electronic form, or other recorded media, are contemplated.

Thus, in a further aspect, the invention provides a kit comprising the above-described compositions and an instruction for using the combination in treating, improving, curing or preventing viral infections.

The appropriate dosage and frequency of treatment may vary depending on the specific symptoms and signs exhibited by the patient, or the clinical situation for prophylactic uses. Other health related factors should also be considered.

DETAILED DESCRIPTION OF PREFERRED EMBODIMENTS

In order that the invention may be better understood, preferred embodiments will now be described by way of example only with reference to the following Examples.

EXAMPLE 1

53 year old male with symptoms of viral upper respiratory infection started experiencing nasal congestion and nasal discharge. Patient sprayed 0.2 ml of Verapamil 2 mg/ml into each nostril and directly into the back of the throat. Within minutes, patient experienced a reduction in nasal congestion and decreased nasal discharge. The nasal continued to slow and stopped after approximately 20 minutes.

After a couple of hours the patient then continued to apply repeated small local applications of 0.1 ml intranasally and orally to throat twice more when the symptoms of nasal congestion started to recurred and again prior to going to sleep that night.

When the patient awoke the next day the upper respiratory symptoms were cleared, but the patient began to experience lower respiratory infectious symptoms of an increasingly productive cough the next day. These lower respiratory symptoms worsened and by the following day the patient was experiencing extreme uncontrolled coughing episodes. The patient went on Verapamil 80 mg q6-8 hours. Prior to starting Verapamil, the patient had profuse clear mucus discharge from the lungs and was experiencing prolonged and frequent coughing spells. After taking his first dose of Verapamil, within 10-20 minutes the patient noticed a profound reduction in coughing and a significant reduction in volume of sputum being cleared from the lungs. Within 30-60 minutes of the first dose, the cough was infrequent and mostly non-productive. For the next four days, whenever the patient went beyond 6-8 hours of last 80 mg dose, he began to experience increasing productive coughing repeatedly demonstrating a relationship between declining serum Verapamil levels and increasing severity of his bronchitis/pulmonary symptoms and each time that the patient took the 80 mg Verapamil tablet there was a dramatic reduction in pulmonary discharge and reduction in coughing for over 6 hours before symptoms.

EXAMPLE 2

Patient A with recurrent cold sores was given Diltizem 100 mg/ml and asked to apply topically at the first signs of a cold sore. The patient observed that in the initial tingling phase prior to the eruption if he applied the cream, the infection could be prevented and if application was delayed until eruption was visible, he could minimize the severity, reduce the size and complete healing clearance would occur in 2-4 days instead of lasting the usual 7 days.

EXAMPLE 3

Patient B with recurrent cold sores was given Verapamil 200 mg/ml and asked to apply at the first signs of a cold sore. The patient observed that in the initial tingling phase if he applied the cream, the infection could be prevented and if application was delayed until eruption was visible, he could minimize the severity, reduce the size and complete healing clearance could occur in 2-4 days instead of lasting the usual 7 days.

EXAMPLE 4

Male patient with a long history of recurrent Genital Herpes was using Diltiazem. When questioned by the inventor about the frequency of recurrences of his genital herpes before and after starting Diltiazem, the patient reported that before he was having several episode per year, and that after starting Diltiazem there had been only about 1-2 episodes per year, that they were much smaller and seemed to heal much quicker when on when Diltiazem.

EXAMPLE 5

HIV patient took Verapamil 240 mg (120 mg of verapamilSR) twice daily for 2 weeks before repeat blood work and showed significant rise in T4 helper counts.

EXAMPLE 6

A 39 year old woman with a three day history of fever, chills, muscle aches and nausea. On the second and third days the patient developed increasing diarrhea. On the morning of the third day the patient was experiencing loose, watery stools with a cramps and lower abdominal pain. Patient had 6 watery bowel movements and was going to the washroom frequently before starting Verapamil 120 mg tablets, taking one every 8 hours. Within one hour of taking the first Verapamil, the abdominal cramping began subsiding and her stools began to become more formed and diarrhea improved.

EXAMPLE 7

Elderly patient with Herpes Zoster infection on the upper left abdomen. Patient took Verapamil 120 mg SR twice daily and noted reduced pain, reduced rash and rapid healing of lesions.

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

EXAMPLE 8

A 54 year old male surgeon with a latex glove allergy. Symptoms of a red eczematous rash develops when he uses latex gloves. This delayed hypersensitivity reaction is prevented by the application of Verapamil 200 mg/ml ointment prior to wearing latex gloves.

Also the chronic rash that occurs from daily expose to latex was seen to improved within hours of the application of verapamil 200 mg/ml ointment.

EXAMPLE 9

64 year old female with Rheumatoid Arthritis and significant pain and disability in her hands noted a significant reduction of pain in her hand within hours of applying Verapamil or Diltiazem ointments. And patient reported improved mobility of joints with sustained applications over several days.

I claim:

1. A method for treating cold sores in a human comprising: topically administering to the said human a therapeutically effective amount of a composition comprising a calcium channel blocker as the active agent, and a pharmaceutically acceptable diluent or carrier, and wherein said calcium channel blocker is verapamil or diltiazem and wherein the composition is a cream.

2. The method for treating cold sores as claimed in claim 1, wherein said calcium channel blocker is verapamil.

3. The method for treating cold sores as claimed in claim 1 wherein said calcium channel blocker is diltiazem.

4. The method for treating cold sores as claimed in claim 1 wherein the concentration of verapamil is 200 mg/ml.

5. The method for treating cold sores as claimed in claim 1 wherein the concentration of diltiazem is 100 mg/ml.

\* \* \* \* \*